(12) United States Patent
Trahanovsky et al.

(10) Patent No.: US 8,383,864 B2
(45) Date of Patent: Feb. 26, 2013

(54) METHOD FOR THE CONVERSION OF CELLULOSE AND RELATED CARBOHYDRATE MATERIALS TO LOW-MOLECULAR-WEIGHT COMPOUNDS

(75) Inventors: Walter S. Trahanovsky, Ames, IA (US); Ronald C. Holtan, Stanhope, IA (US); Kyle W. Quasdorf, Los Angeles, CA (US); Norman K. Olson, Nevada, IA (US); Alyse A. Hurd, Los Angeles, CA (US); Joseph A. Marshall, Plano, TX (US)

(73) Assignee: Iowa State University Research Foundation, Inc., Ames, IA (US)

( * ) Notice: Subject to any disclaimer, the term of this patent is extended or adjusted under 35 U.S.C. 154(b) by 210 days.

(21) Appl. No.: 12/962,770

(22) Filed: Dec. 8, 2010

(65) Prior Publication Data
US 2011/0137085 A1 Jun. 9, 2011

Related U.S. Application Data

(60) Provisional application No. 61/267,619, filed on Dec. 8, 2009.

(51) Int. Cl.
*C07C 45/78* (2006.01)
*C07C 29/74* (2006.01)
(52) U.S. Cl. ........ 568/386; 568/483; 568/868; 568/869; 568/902
(58) Field of Classification Search .................. 568/386, 568/483, 868, 869, 902
See application file for complete search history.

(56) References Cited

U.S. PATENT DOCUMENTS

| 5,562,777 | A | 10/1996 | Farone et al. |
| 6,982,328 | B2 | 1/2006 | Werpy et al. |
| 7,094,932 | B2 | 8/2006 | Marjerski et al. |
| 7,494,637 | B2 | 2/2009 | Peters et al. |
| 7,501,025 | B2 | 3/2009 | Bakker et al. |
| 7,626,006 | B2 | 12/2009 | Pascaly et al. |
| 7,652,131 | B2 | 1/2010 | Werpy et al. |
| 2010/0019192 | A1 | 1/2010 | Suppes et al. |

FOREIGN PATENT DOCUMENTS

| CN | 1276056 C | 9/2006 |
| IT | 1233413 | 2/1987 |
| JP | 2001205070 | 1/2000 |
| JP | 2005-296906 | 10/2005 |

OTHER PUBLICATIONS

Crabtree, S.P. et al., "Optimize Glycol Production From Biomass", Hydrocarbon Processing, Feb. 2006, pp. 87-92.
Fukushima, Yoshiaki, "Application of Supercritical Fluids", R&D Review of Toyota CRDL, vol. 35, No. 1, pp. 1-9, Nov. 8, 1999.
Goto, Motonobu et al., "Supercritical Thermal Decomposition of Cellulose: Experiments and Modeling", Ind. Eng. Chem. Res. 1990, 29, p. 1091-1095.
Graybeal, Judith, "Will Corn (or Something Else) Become the New Oil? Biomass-Derived Products Show Promise", http://www.techcommjournal.org/index.php?articleID=149, printed from Internet Apr. 9, 2009, 2 pages.
Ishikawa, Y. et al., "Chemical Conversion of Cellulose As Treated in Supercritical Methanol", Cellulose 2001, 8:189-195.
Jacoby, Mitch et al., "Chemicals From the Garden: Advances in Biomass Chemistry transform plant matter to valuable products", Science & Technology, www.CEN-ONLINE.ORG, Jul. 6, 2009, pp. 26-28.
Minami, E. et al., "Decomposition Behavior of Woody Biomass in Water-Added Supercritical Methanol", J Wood Sci 2005, 51:395-399.
Minowa, T. et al., "Decomposition of Cellulose and Glucose in Hot-Compressed Water Under Catalyst-Free Conditions", Abstract, http://cat.inist.fr/?aModele=afficheN&cpsidt=2213325, printed from Internet on Apr. 9, 2009, 1 page.
Nobuyuki, Hayashi et al., "Reaction Kinetics of Cellulose Decomposition in Hot-Compressed-Water", http://sciencelinks.jp/j-east/article/200422/000020042204A0789514.php, printed from Internet on Apr. 9, 2009, 1 page.
Saka, Shiro, "Clean and Green Supercritical Fluid Science for Biomass to Fuels and Chemicals", The 2nd Joint International Conference on "Sustainable Energy and Environment (SEE 2006)", Nov. 21-23, 2006, C-034(O), 9 pages.
Saka, Shiro et al., "Useful Products from Lignocellulosics by Supercritical Water Technologies", The 2nd Joint International Conference on "Sustainable Energy and Environment (SEE 2006)", Nov. 1-23, 2006, C-035(P), 5 pages.
Sasaki, Mitsuru et al., "Dissolution and Hydrolysis of Cellulose in Subcritical and Supercritical Water", Ind. Eng. Chem. Res. 2000, 39, p. 2883-2890.
Sominsky, L. et al., "Uncatalyzed Meerwein-Ponndorf-Oppenauer-Verley Reduction of Aldehydes and Ketones under Supercritical Conditions" J.Org. Chem. 2004, 69, 1492-1496.
Watanabe, Masaru et al., "Catalytic Hydrogen Generation from Biomass (Glucose and Cellulose) with $ZrO_2$ in Supercritical Water", Biomass and Bioenergy, 22 (2002), pp. 405-410.
Ehara, Katsunobu et al., "A Comparative Study on Chemical Conversion of Cellulose Between the Batch-Type and Flow-Type Systems in Supercritical Water", Cellulose 9:301-311, 2002.
Kabyemela, Bernard M. et al., "Glucose and Fructose Decomposition in Subcritical and Supercritical Water: Detailed Reaction Pathway, Mechanisms, and Kinetics", Ind. Eng. Chem. Res. 1999, 38, pp. 2888-2895.
Li, Lixiong et al., "Interaction of Supercritical Fluids with Lignocellulosic Materials", Ind. Eng. Chem. Res. 1988, 27, pp. 1301-1312.

(Continued)

*Primary Examiner* — Sikarl Witherspoon
(74) *Attorney, Agent, or Firm* — McKee, Voorhees & Sease, P.L.C.

(57) ABSTRACT

Methods of converting cellulose or related biorenewable carbohydrate materials into high-value chemical compounds. The methods provide a means of converting low-cost materials such as cellulose and biomass into high yields of compounds such as ethylene glycol, propylene glycol, glycerin, methanol, hydroxyacetone, glycolaldehyde and dihydroxyacetone.

22 Claims, 3 Drawing Sheets

OTHER PUBLICATIONS

Maffi, S. et al., "Direct Wood Liquefaction with Hydroalcoholic Hydrogen-Donor Mixtures at SuperCritical Conditions", CHEMECA'88, Australia's Bicentennial International Conference for the Process Industries, Sydney, Aug. 28-31, 1988, 3 pages.

Richards, Geoffrey N., "Glycolaldehyde from Pyrolysis of Cellulose", Journal of Analytical and Applied Pyrolysis, 10 (1987), pp. 251-255.

Sasaki, Mitsuru, "Rapid and Selective Production of Valuable Chemical Intermediates from Cellulose using Supercritical Water", Cellulose Commun., vol. 10, No. 2 (2003), pp. 63-68.

Sasaki, Mitsuru et al., Rapid and Selective Retro-Aldol Condensation of Glucose to Glycolaldehyde in Supercritical Water, Green Chemistry, 2002, 4, pp. 285-287.

Sominsky, Lena et al., "Uncatalyzed Meerwein-Ponndorf-Oppenauer-Verley Reduction of Aldehydes and Ketones under Supercritical Conditions", J. Org. Chem. 2004, 69, pp. 1492-1496.

Vasilakos, Nicholas P. et al., "Hydrogen-Donor Solvents in Biomass Liquefaction", Ind. Eng. Chem. Process Des. Dev. 1985, 24, pp. 304-311.

Yamada, Tatsuhiko et al., "Characterization of the Products Resulting from Ethylene Glycol Liquefaction of Cellulose", J. Wood Sci. (2001) 47:458-464.

METHOD FOR THE CONVERSION OF CELLULOSE AND RELATED CARBOHYDRATE MATERIALS TO LOW-MOLECULAR-WEIGHT COMPOUNDS

CROSS-REFERENCE TO RELATED APPLICATIONS

This application claims priority under 35 U.S.C. §119 to U.S. Provisional Application No. 61/267,619, filed Dec. 8, 2009, which is herein incorporated by reference in its entirety.

FIELD OF THE INVENTION

The invention relates to methods of converting cellulose and related carbohydrate materials to low-molecular-weight compounds, including ethylene glycol, propylene glycol, glycerin, methanol and hydroxyacetone. The invention provides methods for a single step conversion of biomass sources to low-molecular-weight compounds through either batch, campaign-type or continuous processes that do not necessitate hydrogen gas, strong acids, metal catalysts, or enzymes.

BACKGROUND OF THE INVENTION

Biomass is an abundant and renewable resource. As a result of such availability of biomass there is a significant need for improved methods of biomass conversion. There is a vast body of work of others skilled in the art attempting to convert biomass sources into desired, high-value compounds. See for example, U.S. Pat. No. 7,494,637. However, biomass conversion methods have consistently failed to yield high volumes and/or provide efficient methods to convert biomass sources into high-value compounds as has been achieved by the present invention. For example, current industrial production of compounds such as propylene glycol and ethylene glycol require the use of petroleum and do not convert renewable sources. In such methods, ethylene or propylene are epoxidized from alkenes to form oxides which are hydrolyzed to form the ethylene or propylene glycol. As a result, such methods require significant and undesirable dependence on petroleum for the products of these biomass conversion processes.

Methods to efficiently convert biomass sources into these same desired compounds, including propylene glycol and ethylene glycol, would minimize the necessity of petroleum products for the production of commercially useful low-molecular-weight compounds and chemicals. Biomass conversion would further limit the large amounts of cellulosic waste, or biomass, which if not utilized is generally left to decay, either in a landfill or in open fields. Therefore, there is significant demand for the use of renewable starting materials, such as biomass, to produce valuable products as described in the present invention.

Presently, very little biomass is converted into commercially-useful compounds. This is largely due to the fact that conversion of biomass, such as agricultural waste products, is difficult due to the complex structure of plant cell walls. The plant cell wall is made of lignocellulose, which consists approximately of cellulose (38-50%), hemicellulose (17-32%) and lignin (15-30%). These components are difficult to break down as the cellulose is made up of crystalline bundles of polysaccharide chains of β-1,4 bonded glucose molecules. Additionally, the hemicellulose consists of chains of amorphous combinations of the sugar molecules xylose, mannose and arabinose. The final component of lignocellulose is lignin, a macromolecule of substituted phenols acting to bind together the lignocellulose matrix which provides strength to cell walls.

Various methods for converting lignocellulose require the use of catalysts, enzymes, or other expensive ingredients to depolymerize and/or decrystallize the complex structure of the lignocellulose of biomass precluding the development of an efficient and effective one-step conversion process. See M. Jacoby, Chemicals from the Garden, C&EN 26-28 (2009). Strong acids are often used; however, the use of these requires the refining of the cellulosic materials to ensure sufficient contact between the acid and the biomass. See e.g., U.S. Pat. No. 5,562,777. Such methods further result in large amounts of waste products, incurring additional costs.

Therefore, it is an object of the present invention to develop methods of converting cellulose and related carbohydrate materials to commercially-useful low-molecular-weight compounds.

It is a further object of the present invention to develop methods to convert cellulose and related carbohydrate materials to ethylene glycol, propylene glycol, glycerin, methanol, hydroxyacetone, glycolaldehyde and dihydroxyacetone.

A still further object of the present invention is to develop a single step conversion method to produce the low-molecular-weight compounds without the need for hydrogen gas, strong acids, metal catalysts, or enzymes.

BRIEF SUMMARY OF THE INVENTION

The invention overcomes the problems associated with prior art techniques, as well as other problems as will become apparent herein. According to one aspect of the invention, novel methods of converting biomass sources, including both agricultural and municipal waste sources, to finished high-value products in a one-step method are presented. The cellulose and other related carbohydrate materials, such as glucose and other monosaccharide sources, according to the invention generate high yields of ethylene glycol, propylene glycol, glycerin, methanol, hydroxyacetone, glycolaldehyde and dihydroxyacetone. In another aspect of the invention, batch and continuous methods of biomass conversion that do not necessitate the use of catalysts are presented.

According to the invention, a process for cellulose conversion into low-molecular-weight compounds comprises contacting a cellulose or related carbohydrate material source with a low-molecular-weight alcohol to form a reaction mixture in a reactor, heating the reaction mixture under high temperature and pressure conditions for the reaction mixture to undergo thermal decomposition, and converting the cellulose or related carbohydrate material source into low-molecular-weight compounds. According to a preferred embodiment of the invention, the low-molecular-weight alcohol is ethanol, 1-propanol, 1-butanol, 2-butanol or 2-propanol. According to additional embodiments of the invention, the reaction mixture is cooled to enable separation of liquid and solid phases.

According to additional embodiments of the invention, the temperature in the reactor ranges from about 250° C. to about 375° C. and the pressure ranges from about 1000 psi to about 3500 psi. The reaction mixture is heated under high pressure conditions for a period of time between about 20 minutes to about 2 hours. Additionally, the cellulose conversion methods comprise a first conversion step to convert the cellulose or related carbohydrate material source to glucose, a mono- or small oligosaccharide prior to combining with said low-molecular-weight alcohol. According to such embodiment of the invention, the reaction mixture is not sensitive to impurities and does not produce glucoside or levoglucosan products.

According to additional embodiments of the invention, a reaction mixture is heated to a critical temperature and critical pressure to create a supercritical fluid.

A process for producing ethylene glycol, propylene glycol, glycerin, methanol, hydroxyacetone, glycolaldehyde and dihydroxyacetone products from a cellulose or related carbohydrate material source according to the invention comprises contacting a collection of cellulose or related carbohydrate material source with a low-molecular-weight alcohol to form a reaction mixture in a reactor, heating the reaction mixture under critical temperature and pressure conditions to produce ethylene glycol, propylene glycol, glycerin, methanol, hydroxyacetone, glycolaldehyde and dihydroxyacetone products, and separating and collecting the products. According to this embodiment of the invention, the reaction does not require the use of a catalyst.

According to additional embodiments of the invention, the temperature in the reactor ranges from about 250° C. to about 375° C. and the pressure ranges from about 1000 psi to about 3500 psi. An additional embodiment of the invention comprises first converting the cellulose or related carbohydrate material source to glucose, a mono- or small oligosaccharide prior to combining with said low-molecular-weight alcohol. According to such embodiment of the invention, the reaction mixture is not sensitive to impurities and does not produce glucoside or levoglucosan products.

According to the invention, the preferred low-molecular-weight alcohol is ethanol, 1-propanol, 1-butanol, 2-butanol or 2-propanol and temperature and pressure conditions approach or exceed the supercritical temperature and pressure of the low-molecular-weight alcohol.

An additional embodiment of the invention is a continuous process for the conversion of cellulose or related carbohydrate material source to form ethylene glycol, propylene glycol, glycerin, methanol and hydroxyacetone products. The embodiment for a continuous process comprises continuously feeding a reactor a source of cellulose or a related carbohydrate material, combining a low-molecular-weight alcohol to the source of cellulose or a related carbohydrate material to form a reaction mixture, maintaining a constant temperature and pressure condition of the reaction mixture, and separating ethylene glycol, propylene glycol, glycerin, methanol and hydroxyacetone products from the reaction mixture. According to this embodiment of the invention, the temperature and pressure conditions cause thermal decomposition of the reaction mixture and eliminate the need for a catalyst or additional reagents.

According to this embodiment of the invention, the temperature in the reactor is at least about 250° C. and the pressure ranges from about 1000 psi to about 3500 psi. According to an additional embodiment, the reaction mixture is heated to a critical temperature and critical pressure to create a supercritical fluid. The process may further comprise a first conversion step to convert the source of cellulose or related carbohydrate material to glucose, a mono- or oligosaccharide before feeding into the reactor. The process according to this embodiment of the invention results in a reaction mixture that is not sensitive to impurities and does not produce glucoside or levoglucosan products.

These and other embodiments of the invention will be readily apparent based on the disclosure of the present invention.

DETAILED DESCRIPTION OF THE PREFERRED EMBODIMENT

The embodiments of this invention are not limited to particular methods of biomass conversion, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

Unless defined otherwise, all technical and scientific terms used herein have the same meaning as commonly understood by one of ordinary skill in the art to which embodiments of the invention pertain. For example, psi shall mean pound per square inch or pound-force per square inch as is understood by those of skill in the art.

Many methods and materials similar, modified, or equivalent to those described herein can be used in the practice of the embodiments of the invention without undue experimentation, the preferred materials and methods are described herein. In describing and claiming the embodiments of the invention, the following terminology will be used in accordance with the definitions set out below.

The terms "biomass" and "carbohydrate material," as used herein, refers to any source of cellulosic and/or lignin/lignocellulosic biomass, including for example, wood, municipal waste, trees or parts thereof, forest product residues, energy crops, straw, grass, corn, corn husks, paper and paper products, animal, agricultural and human wastes, sewage sludge, and living or dead plants. Accordingly, biomass includes any of wood, cellulose, hemicellulose, lignin, lignocellulosic materials, or mixtures thereof, paper, as well as wastes and residues from forests, animals, and humans, including municipal waste, that are at least partially organic in their makeup, and any plant material or residue of a plant, whether such plant or residue is living or not. As used herein "biomass" and "carbohydrate material" may further include sources of cellulose, glucose and other sources of simple sugars disclosed according to the invention.

The term "cellulose," as used herein, refers to a polysaccharide consisting of a linear chain of several hundred to over ten thousand β(1,4) linked D-glucose units. Cellulose as used herein further refers to any source of cellulosic and/or lignocellosic biomass.

The term "catalyzed," as used herein, refers to the use of any compound, enzyme or other catalyst to increase the rate of a chemical reaction. Biomass conversion often requires the use of enzymatic catalysis, such that an enzyme catalyzes the conversion of a substrate into a product. Alternatively, the depolymerization of cellulose has been catalyzed by combining copper chloride and chromium chloride dissolved in an imidazolium ionic liquid. (C&EN, 87(27):26-28 (2009)).

The term "low-molecular-weight alcohol," as used herein refers to saturated alcohols having one to ten carbon atoms. A low-molecular-weight alcohol according to the invention is a reducing alcohol that is capable of bringing about an uncatalyzed Meerwein-Ponndorf-Verley (MPV) reaction. According to various preferred embodiments of the invention, low-molecular-weight alcohol may include both primary and secondary alcohols, including for example, ethanol, 1-propanol, 1-butanol, 2-butanol and 2-propanol. According to an additional embodiment, low-molecular-weight alcohol may further include cyclic alcohols, such as cyclohexanol, and diols such as 1,5-pentanediol. A preferred embodiment of the invention includes secondary alcohols, such as 2-propanol or isopropyl alcohol, as the low low-molecular-weight alcohol for biomass conversion. However, as one skilled in the art will appreciate, tertiary alcohols, including for example tert-butyl alcohol, do not function as reducing alcohols for MPV reactions and are not suitable for use as a low-molecular-weight alcohol according to the invention.

The term "supercritical alcohol," as used herein refers to an alcohol that becomes a supercritical fluid (SCF). For example, according to the invention, when a low-molecular-weight alcohol, such as 2-propanol, is heated to its critical temperature ($T_c$=235° C.) under its critical pressure ($P_c$=at least 691 psi of pressure), the gas phase and liquid phase merge to form a supercritical fluid. A supercritical fluid or specifically a supercritical alcohol, as may be applicable according to embodiments of the invention, results from a gaseous and liquid portion confined to a limited volume under both elevated temperature and pressure. As such temperature and pressure are increased, gas molecules are forced closer together and the liquid molecules are forced farther apart; resulting in the two phases forming a single SCF phase above a precise critical temperature and critical pressure.

According to embodiments of the invention, an alcohol or fluid may become a supercritical alcohol or SCF upon reaching its critical temperature ($T_c$) and its critical pressure ($P_c$). However, according to alternative embodiments of the invention, the methods of the invention do not necessitate use of a supercritical alcohol or SCF. Temperatures and pressure may be decreased below SCF conditions or may not reach levels to achieve SCF conditions and still yield the desirable results according to the methods of the invention. Therefore, the methods of the invention for converting cellulosic biomass into low-molecular-weight compounds may comprise reacting a collection of biomass with an alcohol, wherein the mixture with the alcohol is heated at high temperatures and under high pressure. According to an alternative or optional embodiment of the invention, such methods may comprise heating the mixture and alcohol to a critical temperature and critical pressure to create a SCF.

The methods of the invention produce two sets of products directly, without the need or use of any catalyst or additional reagents. According to an embodiment of the invention, the methods do not use acids as a reagent for biomass conversion. Beneficially, the use of strong acids is obviated, in addition to the use of catalysts. The use of strong acids is incompatible with the methods of the present invention, as a result of the high temperatures which would be expected to corrode the reactors, namely stainless steel reactors. In the alternative, the methods according to the invention for biomass conversion use alcohols as weak acids under the conditions set forth according to the embodiments of the invention. Therefore, it is an embodiment of the invention that high temperature and pressure conditions permit the use of alcohols rather than strong acids, catalysts or other reagents.

Production of Low Molecular Weight Compounds

According to the invention, the use of a low-molecular-weight alcohol under high pressure and temperature conditions converts cellulose into the following two sets of products: (I) ethylene glycol (EG), propylene glycol (PG), glycerin (GLOL), hydroxyacetone (HYAC) and methanol (MEOL); and (II) alkyl glucosides and levoglucosan. The group I products are approximately 30% weight of the products yielded, whereas the group II products represent approximately 15% weight. The production of group II products has been reported. Minami & Saka, *J Wood Sci,* 51, 395 (2005); Ishikawa & Saka, Cellulose, 8:189-195 (2001) (reporting the conversion of biomass sources using supercritical methanol or other poor reducing alcohols failing to obtain group I products). Notably, the production of group I products in significant yields resulting from simplified chemical conversion methods suitable for industrial scale have not been obtained from prior biomass conversion methods.

According to embodiments of the invention, group I products may further include glycolaldehyde ($HOCH_2$-CHO) and dihydroxyacetone ($HOCH_2$-CO—$CH_2OH$) in significant quantities. The additional group I products are precursors to some of the main group I products and may be produced according to embodiments of the invention in significant yields. According to the invention, such group I products are obtained as a result of first reducing biomass cellulose sources to glucose (or other monosaccharides) and using the alcohols according to the claimed methods. Accordingly, the invention provides high-value compounds, primarily ethylene glycol, propylene glycol, glycerin, hydroxyacetone and methanol in addition to the glucose derivatives alkyl glucosides, and levoglucosan previously obtained from biomass conversion methods.

According to the invention, the biomass and carbohydrate material conversion provides high yields of the high-value compounds, including ethylene glycol, propylene glycol, glycerin, methanol and hydroxyacetone. According to one embodiment of the invention, the highest yields were of ethylene glycol and propylene glycol from the starting materials of biomass and carbohydrate material. The relative high yields of these high-value compounds are notably achieved from inexpensive methods for converting low-cost starting materials, namely cellulose and biomass. The yields achieved according to the methods of the invention are at least comparable or better than the methods of the prior art.

Ethylene glycol and propylene glycol are organic compounds that are commercially important bulk chemicals that may be produced according to the methods of the invention from a biomass source. They are also commercially valuable and sell at higher prices than ethanol products. For example, ethylene glycol (ethane-1,2-diol) is used as antifreeze and in air conditioning units due to its low freezing point and is often a monomer precursor to numerous polymers, including the very important polyester polyethylene terephthalate, which is used in clothing, plastic bottles, etc.

Propylene glycol (propane-1,2-diol) is often used to replace ethylene glycol for applications requiring safer chemical properties, for example in food products. Propylene glycol also has a wide variety of usages, including for example, pharmaceutical solvents, cosmetic applications, toothpastes, mouth wash, a monomer precursor to polymers, including the widely used unsaturated polyester resins, brake and hydraulic fluids, paints and coatings, laundry detergents, pet food, tobacco, shampoos, deodorants, food coloring and flavorings, and less-toxic antifreeze.

Glycerin is an organic compound commonly known as glycerol (1,2,3-propanetriol) and may further be produced according to the methods of the invention from a biomass source. Glycerin is most commonly used as a viscous liquid in pharmaceutical compositions and formulations as a result of its high solubility in water, hygroscopicity, low toxicity and sweet-tasting flavor. Glycerin may be further utilized in food products for preservation and as a bulk chemical and raw material for use in manufacturing mono-glycerides and di-glycerides and numerous other chemical reactions. Glycerin is used in many commonly used products, including cough syrups, toothpaste, shaving cream, soaps, lubricants, and countless other consumer products.

Methanol and hydroxyacetone are also valuable low-molecular-weight products. For example, hydroxyacetone can be readily reduced (utilizing hydrogen and a catalyst) to propylene glycol. Accordingly, the production of glycerin, methanol and hydroxyacetone from a biorenewable source at high yields, according to the methods of the invention, provides numerous benefits to be realized by a skilled artisan.

Additionally, glucose derivatives, including alkyl glucosides and levoglucosan may also be produced according to the methods of the invention when a cellulose, a cellulosic material (such as paper), a lignocellulose material (such as wood), or starch source is utilized. However, according to the invention, once a cellulose or lignocellulosic material is converted to glucose or other monosaccharides before undergoing the reactions of the methods of the invention, the thermal decomposition of monosaccharides produces primarily ethylene glycol, propylene glycol, glycerin, methanol, and hydroxyacetone, rather than the glycosides and levoglucosan.

According to the methods of the invention, the ethylene glycol, propylene glycol, glycerin, methanol, and hydroxyacetone products are more readily and preferably purified than the glucosides, glycosides and/or levoglucosan. According to a preferred embodiment of the invention, use of glucose as a starting material for the methods of this invention result in production of group I products representing approximately 60% weight (rather than estimated 30% weight from the conversion of cellulose).

The use of glucose as a starting material to generate increased yields of the preferred low-molecular-weight compounds ethylene glycol, propylene glycol, glycerin, methanol, and hydroxyacetone can be extended to other monosaccharides and/or small oligosaccharides. Glucose is an aldohexose, six-carbon monosaccharide aldehyde. The same results favoring the increased production of ethylene glycol, propylene glycol, glycerin, methanol, and hydroxyacetone result from the use of fructose (a ketohexose, six-carbon monosaccharide ketone), xylose (an aldopentose, five-carbon monosaccharide aldehyde), sucrose (a non-reducing disaccharide), and other hexoses, pentoses, or oligosaccharides, either aldo keto-, or non-reducing.

According to the invention, reference to glucose as a starting material (or treating a cellulose or related carbohydrate material to form glucose) shall be understood to incorporate the use of other monosaccharides or small oligosaccharides in addition to glucose. The use of xylan (hemicellulose) produces slightly lower yields of the group I products than those obtained from glucose and the xylan does not produce any levoglucosan as a result of its pentose polymer structure.

According to an alternative embodiment of the invention, the glucose from the glucosides could be further utilized to prepare additional ethylene glycol, propylene glycol, glycerin products or purified for a variety of other uses, for example animal foods, cosmetics, etc. as one of ordinary skill in the art would be capable of achieving based upon the invention described herein and is considered within the scope of the invention.

Methods of Cellulose and Related Carbohydrate Material Conversion

According to an embodiment of the invention, methods for converting cellulose or related carbohydrate material sources into high-value, low-molecular-weight compounds may be obtained from a variety of cellulose sources. According to one embodiment of the invention, the cellulose source for conversion may include any biomass source or carbohydrate material. Various exemplary biomass and carbohydrate materials were tested according to the methods of the invention (see Table 1-3).

Selected biomass sources used according to the methods of the invention may first require pretreatment. Pretreatments are necessitated for conversion of cellulose or related carbohydrate materials (such as various forms of biomass), as cellulose is a solid and difficult to pump through the systems for the conversion into the low-molecular-weight compounds according to the invention. Such pretreatments are necessary for hydrolysis to occur in order to hydrolyze the applicable starting material to glucose or other sugars. Further description of pretreatments is disclosed in U.S. Pat. Nos. 5,562,777 and 7,501,025, the disclosure of which are herein incorporated by reference in its entirety.

According to another embodiment of the invention, a pretreatment may alternatively convert a starting material into a monosaccharide, disaccharide, trisaccharide, or chains of saccharides, producing a water soluble starting material for the methods of the invention described herein. According to the invention, the pretreatment of a lignocellulose would yield glucose, pentose and lignin, requiring the preferred removal of lignin prior to following the methods of the invention.

Pretreatment methods, as known by those skilled in the art, may include swelling of the biomass by adding a liquid source to the biomass, for example by addition of water for hydrolysis to occur and to create a water soluble starting product for the methods of the invention. Alternatively, biomass utilized in the methods of the invention may be milled in dry conditions to separate bran from the biomass. Any methods known in the art can be used for the separation of the bran, for example, the bran may be separated by sieves. One skilled in the art will recognize that the particular form of biomass or cellulose selected for use according to the conversion methods of the invention, may require additional handling and conversion considerations. For example, the conversion of paper waste is distinct from agricultural or municipal waste.

Modifications of a pretreatment method in order to adapt to a particular biomass starting material are intended to fall within the scope of the invention as it will be apparent to those skilled in the art the various changes and modifications of the embodiments of the invention to adapt it to various usages and conditions. The use of a pretreatment to hydrolyze the cellulose or biomass to glucose is expected to result in impurities. Beneficially as discovered by the inventors, according to the invention, the methods set forth below are not sensitive to such impurities. Accordingly, glucose sources resulting from a pretreated cellulose or biomass are efficiently converted to the ethylene glycol, propylene glycol, glycerin, methanol and hydroxyacetone products with very small quantities, if any, of glucosides and levoglucosan produced.

Biomass utilized according to the methods of the invention, may require size reduction in addition to a pretreatment. If necessary, any process for reducing the size of biomass may be utilized either before or after any pre-treatment of the biomass, as known according to those skilled in the art; for example, biomass may be reduced by milling to granule sizes as small as less than 1 mm, or preferably to smaller sizes less than 0.8 mm, 0.6 mm, 0.5 mm, 0.4 mm, 0.3 mm, or 0.2 mm. The selection of the preferred particle size of a biomass source may be selected and performed by methods known in the art, including for example by sieves.

According to an embodiment of the invention, biomass is converted to such high-value compounds by thermal decomposition in high boiling solvents wherein the cellulose and lignocellulose of the biomass are heated under high temperature and high pressure conditions. According to another embodiment of the invention, the mixture may include a supercritical alcohol or SCF. According to a particular embodiment, the mixture of a particular carbohydrate material and a low-molecular-weight alcohol are placed in a stainless steel reactor.

According to another embodiment of the invention, the cellulosic material may first be pretreated to enable its break down into glucose or other mono- or small oligosaccharides. Such pretreatment enables the production of the preferred products of ethylene glycol, propylene glycol, glycerin, methanol, and hydroxyacetone rather than the glucosides and levoglucosan, as a result of the initial conversion of the cellulose or carbohydrate material into preferably glucose or other mono- or small oligosaccharides. Therefore, according to a preferred embodiment of the invention, a cellulose or biomass source is first converted to glucose or other mono- or small oligosaccharides prior to undergoing thermal decomposition using high boiling solvents and high pressure conditions.

According to an embodiment of the invention, a low-molecular-weight alcohol, such as 2-propanol, may further contain additives, such as water. The low-molecular-weight alcohol and cellulose or related carbohydrate source are placed in a reactor according to the methods of the invention. Once inside the reactor, the mixture is heated and optionally stirred. The mixture is heated to high temperature conditions, preferably ranging from about 250° C. to about 375° C., more preferably from about 275° C. to about 350° C., most preferably from about 300° C. to about 325° C. The amount of alcohol used in the mixture according to the invention is determined such that the pressure of the system rises to preferably about 1000 psi to about 3500 psi, more preferably about 2000 psi to about 3500 psi at the maximum temperature.

According to an embodiment of the invention, the amount of the low-molecular-weight alcohol used for a reaction may vary. According to a preferred embodiment the low-molecular-weight alcohol is added in a volume sufficient to fill the reactor about half full at room temperature. According to an embodiment of the invention, low-molecular-weight alcohols have a density at room temperature about two times that of the supercritical fluid at 300° C.

In one particular embodiment of the invention a mixture of cellulose and isopropyl alcohol are placed in a reactor and heated above the supercritical temperature (Tc) of the isopropyl alcohol (235° C.) with sufficient quantities of the alcohol to generate pressure above the supercritical pressure of isopropyl alcohol (691 psi). Beneficially, according to the invention, these methods of biomass conversion described herein and apparent to a skilled artisan do not require the use of a catalyst and are not sensitive to impurities.

According to the invention, the methods of biomass conversion do not necessitate the use of any catalysts, providing a significant benefit over biomass conversion methods employed by others requiring catalysts. As a result, according to the invention, the methods of biomass conversion overcome significant burdens faced by those skilled in the art at the time of the invention by eliminating the additional expense of catalysts, eliminating the requirement of removal and/or recycling of catalysts, not producing unwanted byproducts as a result of use of catalysts, eliminating effects of impurities caused by catalysts in the biomass conversion process, etc.

According to one embodiment of the invention, the reaction mixture is heated to elevated temperatures, from a few minutes to several hours. According to embodiments of the invention wherein the methods include an initial conversion of a cellulose or carbohydrate material into glucose or other mono- or small oligosaccharides, the length of time for the reaction is preferably between about 5 minutes to about 2 hours, more preferably between about 20 minutes to about 60 minutes. According to embodiments of the invention wherein the methods do not include pretreatment for the conversion of a biomass or cellulose source, the length of time for the reaction is preferably between about 1 hour to about 4 hours, more preferably between about 1 hour to about 2 hours. However, as one skilled in the art shall ascertain based upon the disclosure of the present invention, modifications of temperature and pressure conditions, among other variables, may further modify the amount of time for the reactions according to the invention. Such variations are intended to be within the scope of the claimed invention.

After heating the mixture to elevated temperatures, from a few minutes to several hours, the reactor is cooled to room temperature to obtain the reaction mixture and the high-value compounds produced by the biomass conversion. To obtain the high-value compounds the solid and liquid phases are separated.

According to one embodiment of the invention, separation of the high-value compounds may occur by distillation to separate out mixtures of the compounds, as the glycols are thermally stable and therefore easily separated from the methanol and hydroxyacetone products by distillation. Pure methanol and hydroxyacetone can be obtained by distillation. This is also a preferred method to physically separate the glycerin products from the ethylene glycol and propylene glycol products without requiring any chemical reaction to separate the products. Further separation of the ethylene glycol from the propylene glycol products may also be done according to more careful distillation.

Additional separation methodologies may be utilized by those skilled in the art. After separation of the high-value compounds, additional steps may be necessitated according to the desired use of the compounds, as will be ascertained by those of ordinary skill in the art, including for example, purification, refining, extraction or other types of processing of the high-value compounds. For example, purification of the compounds may be necessary, such as purification of the propylene glycol if it is to be used in food products.

According to another embodiment of the invention, the cellulose or related carbohydrate material conversion into high-value compounds by thermal decomposition in high boiling solvents, optionally such as supercritical alcohols or SCF, may be done in a batch process, campaign-type process or a continuous process.

Batch processing methods according to an embodiment of the invention include placing the mixture from a particular biomass or carbohydrate material with the low-molecular-weight alcohol into a stainless steel reactor in aliquots. The reactor containing the mixture is heated and stirred to reach a temperature that may range from about 250° C. to about 375° C. and pressure of from about 1000 psi to about 3500 psi at the maximum temperature, more preferably from about 275° C. to about 355° C., most preferably from about 300° C. to about 325° C. and pressure from about 2000 psi to about 3500 psi at the maximum temperature. The mixture is heated and stirred for a sufficient period of time, ranging from a few minutes to several hours in order to obtain the desired high-value compounds.

According to an embodiment of the invention, the batch processing requires the reactor be cooled down and the pressure reduced between batches. Once the reactor is cooled, then high-value compounds may be obtained from the reactor. According to one embodiment of the invention, the reactor is operated at about 300° C. and about 2000 psi, which would require cooling down and lowering the pressure to approximately room temperature (about 30° C.) and approximately one atmosphere (about 14.5 psi) before running another batch through the reactor. Such a process may take hours for a large reactor or alternatively may take approximately an hour for a small reactor to cool to these temperature conditions and decrease the pressure.

Alternatively, a series of smaller batches or campaign-type process may be utilized under the methods of the invention to provide for enhanced methods of increased production of the ethylene glycol, propylene glycol, glycerin, methanol, and hydroxyacetone. According to an embodiment of the invention, a campaign-type process involves the solvent and starting materials (such as glucose, cellulose, or a biomass source) being pumped into a reactor. The reactor is heated and the reaction is run under high pressure. After allowing time for the reaction to take place, the reaction mixture is drained from the reactor with cooling and pressure reduction. After the reaction mixture is removed from the reactor, the reactor is recharged with solvent and starting material and the process continues without the need to cool the reactor before a subsequent campaign reaction is initiated.

According to certain embodiments of the invention, particularly suitable conditions for campaign-type processes include the use of an initially cool reactor, adding a low-molecular weight alcohol (such as 2-propanol), heating the reactor to about 275° C. to about 325° C., pumping in the starting material to run the reaction mixture under high pressure from about 1000 psi to about 3500 psi, draining the products and cooling the products at the end of the reaction time. Subsequent batches may be run according to the same methods while using the high temperature reactor, without the need to cool the reactor and re-heat the reactor for each subsequent batch. According to the embodiments of the invention, campaign-type process generated the same group I products achieved from both batch and continuous processes and obtained similar yields of the products.

An additional embodiment of the invention is a continuous process for methods of biomass conversion according to the invention to obtain ethylene glycol, propylene glycol, glycerin, methanol, and hydroxyacetone. According to an embodiment of the invention, a continuous process involves the starting material (such as glucose, cellulose or a biomass source) and low-molecular weight alcohol mixture being passed through a heated chamber allowing the mixture to reach the high temperature and high pressure needed according to the invention. The reaction mixture is pumped under high pressure continuously through a chamber that is under high temperature conditions. The continuous pumping of the reaction mixture through the heated and pressurized chamber lasts for a sufficient amount of time to allow the reaction to reach completion. Thereafter, the reaction mixture flows out of the chamber with cooling and pressure reduction. The reaction mixture is then collected and the products are separated.

According to a preferred embodiment of the invention, a reaction mixture of glucose and 2-propanol is continuously pumped through a chamber that is heated to a temperature from about 275° C. to about 325° C. and under high pressure from about 1000 psi to about 3500 psi. The reaction mixture remains under the high pressure and high temperature conditions in the chamber for a few minutes to several hours, to ensure the reaction to form the group I products is completed. Then the reaction mixture with the group I products flows out of the chamber for cooling and pressure reduction to separate and obtain the group I products.

According to either of the embodiments of a campaign-type process and/or a continuous process, the need to stop and cool the reactor and bring it to normal pressure conditions as described for a batch process is eliminated. Beneficially, the high-value group I compounds are more efficiently generated without stopping to cool the temperature and/or reduce the pressure. Therefore, a series of smaller batches or the continuous process is advantageous in that it does not require the inactivation of the reactor to open and remove the high-value compounds produced by the methods of the invention. Rather, either provides a means for continuously removing generated product from the reactor.

Benefits of utilizing a campaign-type process or a continuous process include increased product yield, including yield consistency and quality, reduction of manufacturing costs and reduction of waste products, all providing an efficient and cost-effective commercial process for making the high-value compounds according to the invention. Additionally, use of a campaign-type process or a continuous process yields safer methods, in addition to more efficient methods, as a result of the ability to process relatively smaller amounts at a continuous pace. Therefore, the use of larger batches to generate industrial amounts of the high-value compounds with the batch process is efficiently replaced with either a series of smaller batches or the continuous process.

Those of skill in the art may implement modifications and changes to effectuate the continuous process described herein according to the methods of the invention. This and other optimization of a process is within the skill of the artisan and is incorporated within the scope of the invention.

EXAMPLES

Embodiments of the invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein this patent application is incorporated herein by reference in its entirety.

Example 1

Reaction of cellulose and 2-propanol: A magnetic stirring bar, a 3 g quantity of cellulose, and 150 mL of a mixture of 5% water in 2-propanol were placed in a 300 mL stainless steel reactor (fitted with a pressure gauge and rated to hold pressures up to 4200 psi). The reactor top was bolted on, and the reaction chamber was flushed with argon and then closed. The reaction vessel is then heated. The vessel and contents should be heated to temperatures from 275° C. to 375° C. for a period of time from 30 minutes to several hours. The vessel is also exposed to high pressure conditions, such that the pressure of the reaction chamber reaches from 1500 to 3500 psi. According to a preferred method, the vessel is heated to 325° C. and held at that temperature for at least 1 hour to bring the pressure of the 325° C. chamber to approximately 2000 psi.

The reaction vessel is then allowed to cool to room temperature, and gas samples are collected from the reaction vessel. The top of the reactor is removed, and the reaction mixture is transferred to a centrifuge tube and centrifuged to separate the liquid and solid phases of the mixture, and amounts (5 mg dry weight) of sediment are obtained. The reaction solution is then analyzed by NMR. The solvent and volatile products are removed on a rotary evaporator, and according to an exemplary reaction of cellulose and 2-propanol, approximately 2.7 g of a thick oil is obtained (containing a small amount of 2-propanol). This material is analyzed by NMR.

For quantitative NMR analysis, sodium benzoate is used as the standard. The yields of ethylene glycol, propylene glycol, glycerol, isopropyl glucosides, and levoglucosan are determined in the thick oil. The yields of methanol and hydroxyacetone and acetone are determined in the initial reaction solution. The combined weights of the products derived from cellulose according to an exemplary run of the methods of the invention are approximately 1.5 g. The gases, CO and CO2, are analyzed by gas chromatography.

The following equation summarizes this reaction:

The ethylene glycol and propylene glycol are hypothesized to result from retro-aldol reactions that produce reactive aldehydes from fragmented glucose (these reactions have been observed for glucose in supercritical water; Sasaki, M. et al., Green Chemistry 2002, 4, 285-287). The aldehydes are rapidly reduced due to the interception of the aldehydes by the 2-propanol or ethanol in a non-catalyzed Meerwein-Ponndorf-Verley (MPV) reduction reaction (there are a few reports of these reactions using supercritical 2-propanol, e.g., Sominsky et al., TOC, 2004, 69, 1492). The reduction of the aldehydes in the MPV reaction results in glycols, a significantly more stable product than the aldehydes. This reaction is temperature dependent, preferring temperatures above 275° C. The MPV reaction normally requires a catalyst to reduce the carbon-oxygen double bond of a hydroxy group; however, according to the benefits of the invention no catalyst is required. The production of acetone in the reactions, as expected for an MPV reaction, is consistent with this process when 2-propanol is the solvent; acetaldehyde is produced when ethanol is the solvent. The hydroxyacetone is hypothesized to be an intermediate in the conversion of dihydroxyacetone to propylene glycol.

The reactions described herein may be further illustrated according to the following chemical reactions:

-continued

Example 2

For several runs, the recovery of the carbon from the carbohydrate material was greater than approximately 80%. The various materials utilized include the following:

| Materials | |
|---|---|
| Material | Source |
| Cellulose, Avicel-PH200 | FMC Corporation |
| Cellulose, 20 micron | Sigma-Aldrich |
| Xylan (oat spelt) | Sigma-Aldrich |
| 2-propanol, HPLC grade | Fisher-Scientific |
| D-glucose, ACS grade | Fisher-Scientific |
| Starch | Fisher-Scientific |
| Xylose | Fisher Scientific |
| Filter paper, ground | Whatman Inc. |
| Fructose (99%) | commercial sample |
| Oak flour | local (BECON) |
| Dried Distiller's Grain and Solubles (DDGS) | local (BECON) |
| Corn Stover | local (BECON) |
| Ethanol | AAPER |
| Methanol | Fisher-Scientific |
| Sucrose | Fisher-Scientific |

Various low-molecular-weight alcohols, in addition to 2-propanol, were utilized in this procedure to convert cellulosic materials to low-molecular-weight compounds, including for example ethylene glycol and propylene glycol. Such low-molecular-weight alcohols include, but are not limited to, 1-propanol, 1-butanol, 2-butanol and ethanol.

A summary of various yields of products according to the methods of the invention generated from cellulose and other carbohydrates materials is presented in Table 1. The amounts of starting material ranged from about 1 to 6 grams. The temperatures ranged from 300° C. to 375° C.; pressure, if determined, ranged from 2000 psi to 3500 psi; and the time of reactions spanned one to several hours.

TABLE 1

Reactions of 2-Propanol with Cellulose and Related Carbohydrates[a]

| Products:[b] | Cellulose Avicel | Cellulose Avicel | Cellulose Aldrich | Cellulose Aldrich | Filter paper | Corn stover | Oak flour |
|---|---|---|---|---|---|---|---|
| ethylene glycol | 0.175 | 0.192 | 0.160 | 0.155 | 0.148 | 0.023 | 0.037 |
| propylene glycol | 0.077 | 0.072 | 0.064 | 0.066 | 0.072 | 0.028 | 0.031 |
| glycerol | [c] | [c] | [c] | [c] | [c] | [c] | [c] |
| isopropyl glucoside | 0.053 | 0.088 | 0.087 | 0.073 | 0.048 | 0.003 | 0.025 |
| levoglucosan | 0.071 | 0.090 | 0.078 | 0.075 | 0.025 | 0.003 | 0.006 |
| hydroxyacetone | 0.001 | 0.013 | 0.013 | 0.016 | 0.032 | 0.007 | 0.009 |
| methanol | 0.034 | 0.035 | 0.026 | 0.015 | 0.017 | 0.010 | 0.011 |
| carbon monoxide | 0.008 | 0.006 | 0.012 | 0.015 | 0.027 | 0.026 | 0.028 |
| carbon dioxide | 0.009 | 0.008 | 0.011 | 0.014 | 0.024 | 0.046 | 0.029 |
| Sediment[d] | 0.001 | 0.002 | 0.005 | 0.002 | 0.022 | 0.217 | 0.061 |
| Unidentified products[e] | 0.299 | 0.301 | 0.310 | 0.285 | 0.319 | 0.390 | 0.484 |
| Total products[f] | 0.412 | 0.491 | 0.428 | 0.430 | 0.341 | 0.074 | 0.119 |
| acetone[g] | 0.549 | 0.428 | 0.407 | 0.117 | 0.360 | 0.136 | 0.202 |

| Products:[b] | Xylan (oat) | DDGS | Starch | Glucose | Glucose | Xylose | Fructose |
|---|---|---|---|---|---|---|---|
| ethylene glycol | 0.007 | 0.018 | 0.076 | 0.289 | 0.255 | 0.259 | 0.141 |
| propylene glycol | 0.016 | 0.050 | 0.053 | 0.149 | 0.112 | 0.131 | 0.134 |
| glycerol | [c] | [c] | [c] | 0.064 | 0.080 | 0.085 | 0.105 |
| isopropyl glucoside | 0.011 | 0.000 | 0.065 | [c] | [c] | [c] | [c] |
| levoglucosan | 0.000 | 0.001 | 0.104 | [c] | [c] | [c] | [c] |
| hydroxyacetone | 0.036 | 0.008 | 0.013 | 0.012 | 0.052 | 0.079 | [h] |
| methanol | 0.002 | 0.002 | 0.010 | 0.065 | 0.070 | 0.077 | [h] |
| carbon monoxide | 0.032 | 0.014 | 0.004 | 0.010 | [h] | [h] | [h] |

TABLE 1-continued

Reactions of 2-Propanol with Cellulose and Related Carbohydrates[a]

| carbon dioxide | 0.049 | 0.047 | 0.005 | 0.011 | [h] | [h] | [h] |
|---|---|---|---|---|---|---|---|
| Sediment[d] | 0.133 | 0.087 | 0.102 | 0.001 | [h] | [h] | [h] |
| Unidentified products[e] | 0.321 | 0.483 | 0.030 | 0.155 | 0.243 | 0.220 | 0.193 |
| Total products[f] | 0.071 | 0.079 | 0.331 | 0.600 | 0.570 | 0.631 | 0.380 |
| acetone[g] | 0.091 | 0.084 | 0.313 | 0.646 | 0.640 | 0.615 | [h] |

[a]all reactions in 2-propanol or 2-propanol/water
[b]all yields given in grams per gram starting material
[c]amount is too small to determine by NMR
[d]unidentified products not soluble in alcohol
[e]unidentified products soluble in alcohol
[f]Total identified products derived from carbohydrate material. For several runs, the recovery of the carbon from the carbohydrate material was determined to be >80%.
[g]produced by the oxidation of 2-propanol
[h]not determined

Example 3

Various batch reactions using the Materials of Example 2 were completed. Table 2 presents the yields of products according to the methods of the invention generated from several simple sugars. In these runs aqueous solutions of the sugar at room temperature were pumped into the hot alcohol under pressure.

TABLE 2

Reaction of 2-Propanol/Water with Sugars[a]

| Products:[b] | Glucose | Glucose | Fructose | Sucrose |
|---|---|---|---|---|
| ethylene glycol | 0.268 | 0.329 | 0.209 | 0.225 |
| propylene glycol | 0.062 | 0.071 | 0.082 | 0.051 |
| glycerol | 0.063 | 0.076 | 0.083 | 0.071 |
| isopropyl glycolate[c] | 0.036 | 0.038 | 0.029 | 0.026 |
| isopropyl acetate[d] | — | — | — | 0.019 |
| hydroxyacetone | 0.086 | 0.092 | 0.116 | 0.066 |
| methanol | 0.064 | 0.080 | 0.121 | 0.063 |
| Sediment[e] | 0.001 | 0.001 | 0.000 | 0.002 |
| Unidentified products[f] | 0.146 | 0.152 | 0.146 | 0.262 |
| Total products[g] | 0.579 | 0.685 | 0.638 | 0.521 |
| Acetone[h] | 0.518 | 0.619 | 0.621 | 0.529 |

[a]all reactions in 2-propanol/5% water
[b]all yields given in grams per gram starting material
[c]isopropyl ester tentatively assigned as isopropyl glycolate
[d]isopropyl ester tentatively assigned as isopropyl acetate
[e]unidentified products not soluble in alcohol
[f]unidentified products soluble in alcohol
[g]total identified products derived from carbohydrate material
[h]produced by the oxidation of 2-propanol

Example 4

Continuous reactions using the Materials of Example 2 were completed. The yields of products obtained from a continuous run are presented in Table 3. A reaction mixture under high pressure (from approximately 1500 psi to 3500 psi) was pumped sequentially through a high temperature zone (from approximately 200° C. to 325° C.), a heat exchanger, a back-pressure regulator, and then into a collection vessel. The reaction mixture was generated by pumping an aqueous solution of glucose at room temperature into a heated source of 2-propanol (temperature from approximately 275° C. to 325° C.) which was being pumped into the high temperature zone.

TABLE 3

Reaction of 2-Propanol/Water with Glucose in a Continuous Reactor[a]

| Products:[b] | Amount |
|---|---|
| ethylene glycol | 0.087 |
| propylene glycol | 0.000 |
| glycerol | 0.000 |
| glycolaldehyde[c] | 0.098 |
| isopropyl glycolate[d] | 0.025 |
| isopropyl acetate[e] | 0.014 |
| hydroxyacetone | 0.107 |
| dihydroxyacetone | 0.050 |
| methanol | 0.023 |
| sediment[f] | 0.000 |
| unidentified products[g] | 0.299 |
| identified products:[h] | 0.405 |
| acetone[i] | 0.199 |

[a]Continuous reaction pumped through a stainless steel tube having about a 5 min residence time and a length to diameter ratio of about 20. Temperature was 300° C., and the sample was collected over a period of 18 min. Glucose input during this time was 0.64 g and solvent included 32 mL of 2-propanol/5% water.
[b]all yields given in grams per gram starting material
[c]Detected by NMR in the D$_2$O solution as the hydrate but reported as the aldehyde.
[d]isopropyl ester tentatively assigned as isopropyl glycolate
[e]isopropyl ester tentatively assigned as isopropyl acetate
[f]unidentified products not soluble in alcohol
[g]unidentified products soluble in alcohol
[h]total identified products derived from carbohydrate material
[i]produced by the oxidation of 2-propanol The continuous reaction of Example 4 produced significant amounts of glycolaldehyde, hydroxyacetone, and dihydroxyacetone in addition to the production of ethylene glycol, propylene glycol, and glycerol. Although not intending to be limited to a particular theory, it is apparent that the mild conditions resulted in the production of lesser quantities of the ethylene glycol, propylene glycol, and glycerol. The continuous reaction generates greater yields of the group I products, namely ethylene glycol, propylene glycol, and glycerol under higher temperature conditions and/or slower flow rates.

Example 5

Various embodiments of reactors may be used according to the invention, including batch, campaign and continuous systems. Non-limiting examples of such systems are shown, respectively, in FIGS. 1-3.

Figure 1:
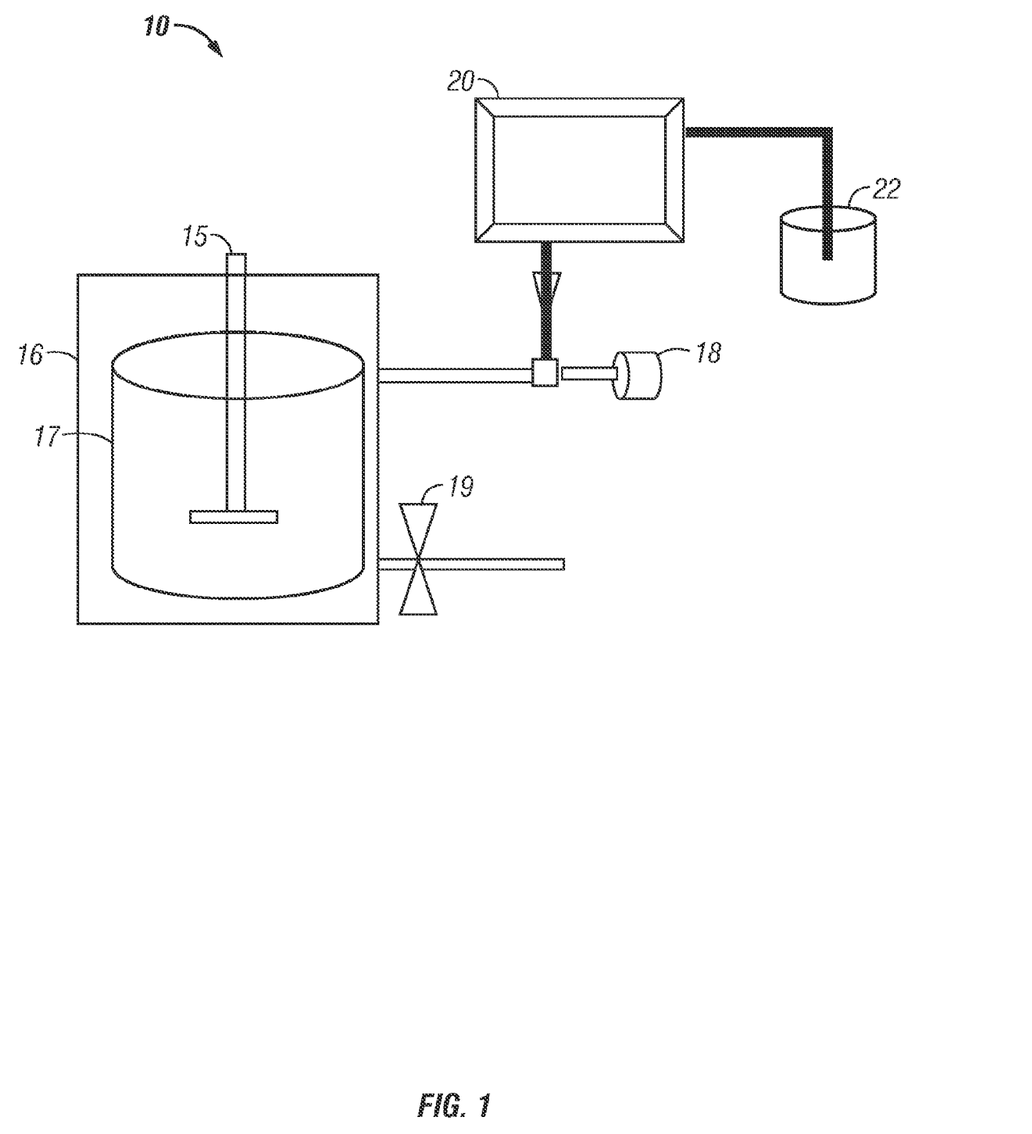
FIG. 1 shows a diagram of a non-limiting embodiment of a batch reactor for use according to the invention.
Figure 2:
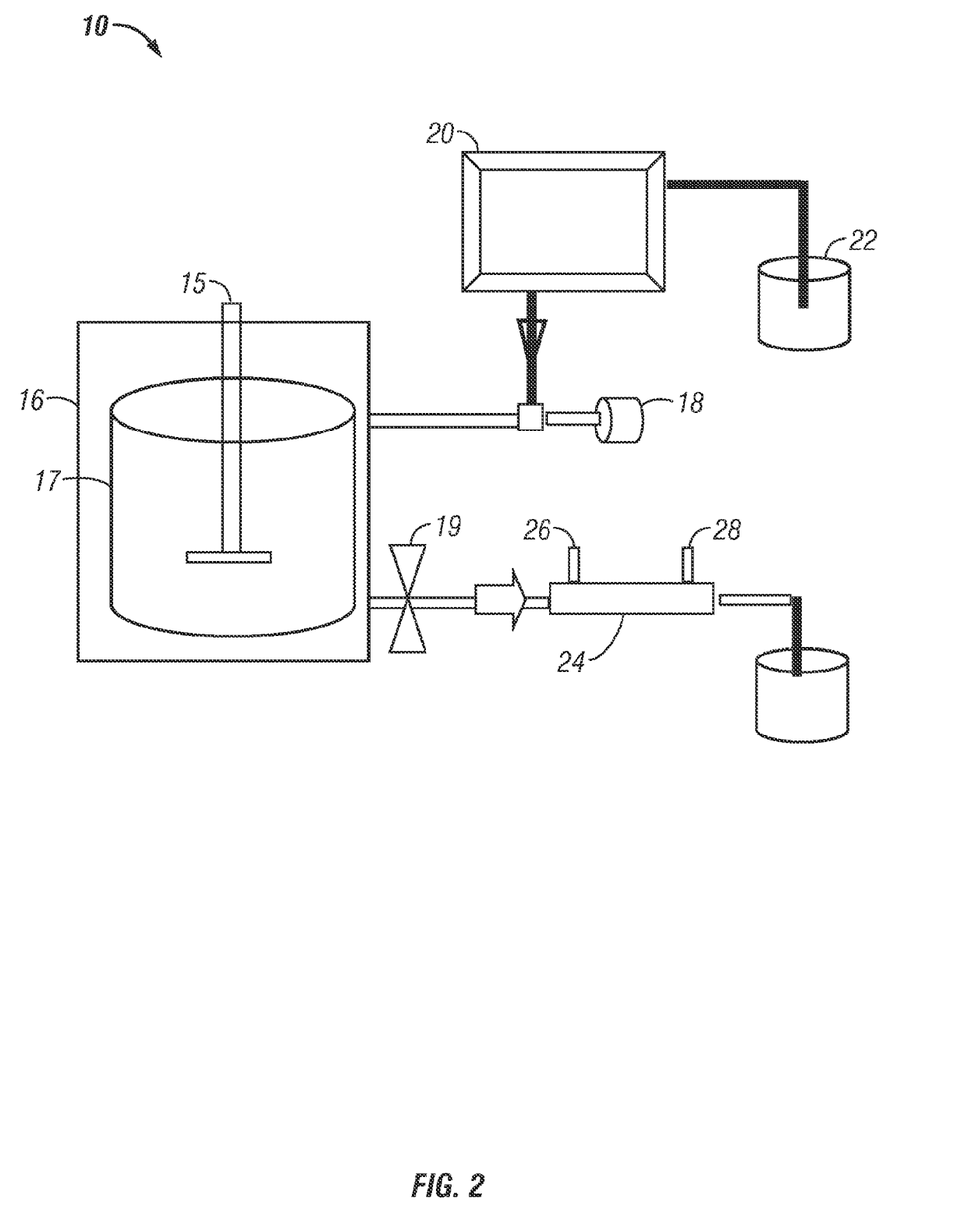
FIG. 2 shows a diagram of a non-limiting embodiment of a campaign reactor for use according to the invention.
Figure 3:
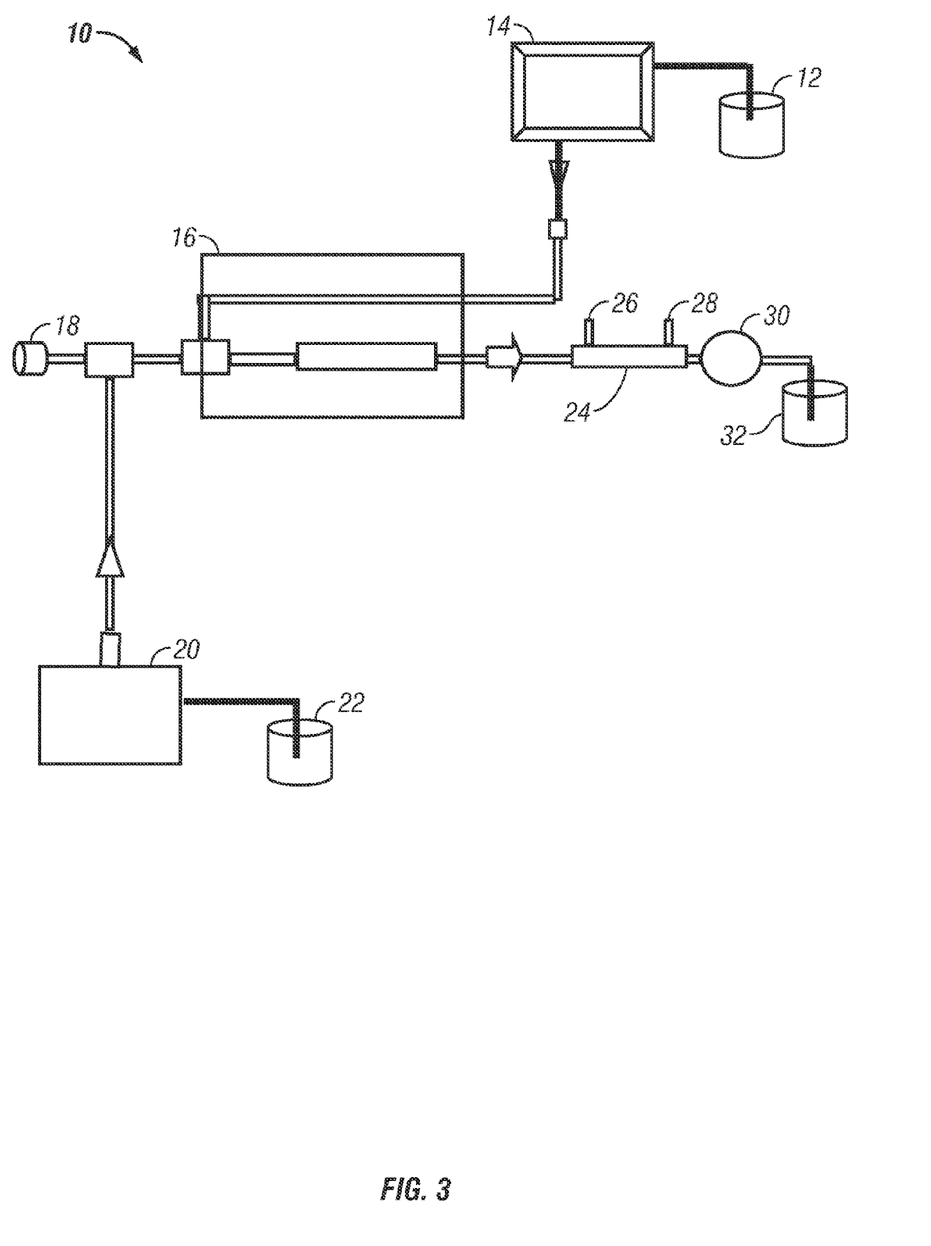
FIG. 3 shows a diagram of a non-limiting embodiment of a continuous reactor for use according to the invention.

Regardless of the reactor system 10 utilized for the methods according to the invention, the following reaction steps occur: (1) cellulose or biomass is reacted in supercritical alcohol (or low-molecular-weight alcohol) to break down to smaller saccharide fragments and produce retro-aldol products (glycolaldehyde, glyceraldehyde, formaldehyde), wherein the retro-aldol products can be converted to dihydroxyacetone and possibly pyruvaldehyde by isomerization and dehydration reactions, including the subset of reactions of retro-aldol reactions of sugars; (2) retro-aldol products react with the solvent by MPV reaction to give glycols and glycerol plus methanol from formaldehyde. According to the embodiments of the invention, the methods of producing low-molecular-weight compounds from biomass or other cellulose materials combine the retro-aldol reactions followed by uncatalyzed MPV reactions to produce high yields of ethylene glycol and related group I products. The production of ethylene glycol and related group I products does not require hydrogenolysis using hydrogen and/or a catalyst to form propylene glycol and ethylene glycol.

According to an embodiment of the invention, a reactor system 10 suitable for batch reactions may comprise, consist of or consist essentially of a reactor 17 housing a heater 16 and agitator 15. A feed pump 20 is in fluid connection with the reactor 17 and provides a feed source 22 to the system. An outlet valve 19 is connected to the reactor 17 contained within the heater 16 in order to remove the low-molecular-weight products produced according to the methods of the invention. Optionally, a rupture disc 18 may be included in the system.

According to a further embodiment of the invention, a reactor system 10 suitable for campaign reactions may comprise, consist of or consist essentially of a reactor 17 housing a heater 16 and agitator 15. An outlet valve 19 is connected to the reactor 17 contained within the heater 16 in order to remove the low-molecular-weight products produced according to the methods of the invention. A feed pump 20 is in fluid connection with the reactor 17 and provides a feed source 22 to provide raw materials to the system. Optionally, a rupture disc 18 may be included in the system. In addition, according to an embodiment of the invention using a campaign reation, a heat exchanger 24 is in connection with the outlet valve 19 and has means for coolant exit 26 and coolant entrance 28 to the system.

According to an additional embodiment of the invention, a reactor system 10 suitable for continuous reactions may comprise, consist of or consist essentially of a reactor 17 housing a heater 16 and agitator 15. A feed pump 20 is in fluid connection with the reactor 17 and provides a feed source 22 to the system. In addition, a solvent pump 14 is in fluid connection with the reactor 17 and provides a solvent source 12 to the system. In addition, according to an embodiment of the invention using a continuous reation, a heat exchanger 24 is in connection with the heater 16 and has means for coolant exit 26 and coolant entrance 28 to the system. Optionally, a rupture disc 18 and a backpressure regulator 30 may be included in the system, wherein a backpressure regulator 30 may be in connection with an outlet 32 for the low-molecular-weight products produced according to the methods of the invention.

Variations and derivations to the reaction systems according to the invention may be made within the scope of the invention. For example various materials may be used for the reactor systems, various options for a heater, such as using a heated ceramic jacket or a liquid medium, etc. Suitable materials include corrosion-resistant materials, such as stainless steel. One skilled in the art will ascertain various modifications that can be made to the shape, size and formation of the reaction systems according to the invention, including for example modifications to the means used for agitation and heating and/or length and shape of components of the reactor systems. The exemplary systems shown in FIGS. 1-3 are non-limiting examples of the systems according to the invention.

What is claimed is:

1. A process for conversion of cellulose or related carbohydrate materials into low-molecular-weight compounds comprising:
    contacting a cellulose or related carbohydrate material source with a low-molecular-weight alcohol to form at reaction mixture in a reactor;
    heating said reaction mixture under high temperature and pressure conditions for said reaction mixture to undergo thermal decomposition; and
    converting said cellulose or related carbohydrate material source into low-molecular-weight compounds, wherein the low-molecular-weight compounds are ethylene glycol, propylene glycol, glycerin, hydroxyacetone, methanol, glycolaldehyde and/or dihydroxyacetone, and wherein said reaction does not use a catalyst.

2. The process according to claim 1, wherein said low-molecular-weight alcohol is ethanol, 1-propanol, 1-butanol, 2-butanol or 2-propanol.

3. The process according to claim 1, wherein said reaction mixture is cooled to separate a liquid phase and a solid phase.

4. The process according to claim 1, wherein the temperature in said reactor is from about 200° C. to about 375° C.

5. The process according to claim 1, wherein the pressure in said reactor is from about 1000 psi to about 3500 psi.

6. The process according to claim 1, wherein said mixture is heated in said reactor for as period of time between about 20 minutes to about 2 hours.

7. The process according to claim 1, further comprising the separation and collection of the low-molecular-weight compound ethylene glycol.

8. The process according to claim 1, further comprising the separation and collection of the low-molecular-weight compound propylene glycol.

9. The process according to claim 1, further comprising first converting said cellulose or related carbohydrate material source to glucose, a mono- or small oligosaccharide prior to combining with said low-molecular-weight alcohol, and wherein said reaction mixture is not sensitive to impurities and does not produce glucoside or levoglucosan products.

10. The process according to claim 1, further comprising the separation and collection of the low-molecular-weight compounds glycerin, methanol and hydroxyacetone.

11. The process according to claim 1, wherein said reaction mixture is heated to a critical temperature and critical pressure to create a supercritical fluid.

12. A process for producing ethylene glycol, propylene glycol, glycerin, methanol, hydroxyacetone, glycolaldehyde and dihydroxyacetone products from a cellulose or related carbohydrate material source comprising:
    contacting a collection of cellulose or related carbohydrate material source with a low-molecular weight alcohol to form a reaction mixture in a reactor;
    heating said mixture under critical temperature and pressure conditions to produce said ethylene glycol, propylene glycol, glycerin, methanol, hydroxyacetone, glycolaldehyde and dihydroxyacetone products, wherein said reaction does not a catalyst; and
    separating and collecting said products.

13. The process according to claim 12, wherein the temperature in said reactor is from about 200° C. to about 375° C.

14. The process according to claim 12, wherein the pressure in said reactor is from about 1000 psi to about 3500 psi.

15. The process according, to claim 12, further comprising first converting said cellulose or related carbohydrate material source to glucose, a mono- or small oligosaccharide before combining with said low-molecular-weight alcohol, and wherein said reaction mixture is not sensitive to impurities and does not produce glucoside or levoglucosan products.

16. The process according to claim 12, wherein said low-molecular-weight alcohol is ethanol, 1-propanol, 1-butanol, 2-butanol or 2-propanol, and wherein said temperature and pressure conditions approach or exceed the supercritical temperature and pressure of said low-molecular-weight alcohol.

17. A continuous process for the conversion of cellulose or related carbohydrate material source to form ethylene glycol, propylene glycol, glycerin, methanol and hydroxyacetone products comprising:
   continuously feeding a reactor a source of cellulose or a related carbohydrate material;
   combining a low-molecular-weight alcohol to said source of cellulose or a related carbohydrate material to form a reaction mixture;
   maintaining a constant temperature and pressure condition of said reaction mixture in said reactor, wherein said temperature and pressure conditions cause thermal decomposition of said reaction mixture and do not employ a catalyst or additional reagents; and
   separating, ethylene glycol, propylene glycol, glycerin, methanol and hydroxyacetone products from said reaction mixture.

18. The process according to claim 17, wherein the temperature in said reactor is at about 200° C. to about 375° C. and the pressure is from about 1000 psi to about 3500 psi.

19. The process according to claim 17, wherein said reaction mixture is heated to a critical temperature and critical pressure to create a supercritical fluid.

20. The process according to claim 17, further comprising first converting said source of cellulose or related carbohydrate material to glucose, a mono- or oligosaccharide before feeding into said reactor.

21. The process according to claim 20, wherein said reaction mixture is not sensitive to impurities and does not produce glucoside or levoglucosan products.

22. The process according to claim 17, wherein glycolaldehyde and dihydroxyacetone products are further produced and separated from said reaction mixture.

* * * * *

UNITED STATES PATENT AND TRADEMARK OFFICE
CERTIFICATE OF CORRECTION

PATENT NO. : 8,383,864 B2
APPLICATION NO. : 12/962770
DATED : February 26, 2013
INVENTOR(S) : Walter S. Trahanovsky et al.

Page 1 of 1

It is certified that error appears in the above-identified patent and that said Letters Patent is hereby corrected as shown below:

In the Claims:

Column 20, claim 1, line 6:
DELETE after form "at"
ADD after form --a--

Column 20, claim 6, line 27:
DELETE after for "as"
ADD after for --a--

Column 20, claim 12, line 58:
ADD after not --use--

Column 20, claim 13, line 61:
DELETE the "." after 200° C

Column 22, claim 18, line 5:
DELETE the "." after 200° C
DELETE the "." after 375° C Signed and Sealed this
Twenty-first Day of May, 2013

Teresa Stanek Rea
*Acting Director of the United States Patent and Trademark Office*